United States Patent [19]
Petrus

[11] Patent Number: 5,875,798
[45] Date of Patent: Mar. 2, 1999

[54] THERAPEUTIC TOOTHPICK FOR TREATING ORAL AND SYSTEMIC DISEASES

[75] Inventor: Edward J. Petrus, Austin, Tex.

[73] Assignee: Advanced Medical Instruments, Inc., Austin, Tex.

[21] Appl. No.: 85,767

[22] Filed: May 28, 1998

Related U.S. Application Data

[63] Continuation-in-part of Ser. No. 935,841, Sep. 23, 1997.

[51] Int. Cl.$^6$ .................................................. A61C 15/00
[52] U.S. Cl. .......................... 132/321; 132/329; 424/49
[58] Field of Search ..................................... 132/321, 323, 132/324, 325, 326, 327, 328, 329; 424/49, 52, 54, 401, 435, 443; 433/215, 217.1

[56] References Cited

U.S. PATENT DOCUMENTS

| | | |
|---|---|---|
| D. 335,934 | 5/1993 | Howard . |
| D. 358,682 | 5/1995 | Johnson . |
| 3,913,596 | 10/1975 | Stuart . |
| 4,218,434 | 8/1980 | Rolla et al. ................................ 424/49 |
| 4,304,245 | 12/1981 | Lichfield . |
| 4,846,200 | 7/1989 | Wiley . |
| 4,986,288 | 1/1991 | Kent et al. ................................ 132/321 |
| 5,002,077 | 3/1991 | Wiley . |
| 5,213,615 | 5/1993 | Michl ........................................ 424/435 |
| 5,230,356 | 7/1993 | Villas ........................................ 132/329 |
| 5,503,842 | 4/1996 | Fazan et al. ............................. 424/443 |
| 5,665,333 | 9/1997 | Homola et al. ........................... 424/54 |
| 5,704,388 | 1/1998 | Freeman . |

OTHER PUBLICATIONS

Sternberg S. Chronic Tooth Infections Can Kill More Than Smile. USA Today Apr. 14, 1998.

Sharpe R. FDA Expected to Approve New Drug From CollaGenex to Fight Gum Disease. Wall Street Journal Oct. 1, 1998.

Murtomaa H, Meurman JN: Mechanical Aids In The Prevention of Dental Diseases in the Elderly, International Dental Journal 1992 Oct. 42(5):365–72.

Kashani H, Birkhed D, Peterson LG: Uptake and Release of Fluoride from Birch and Lime Toothpicks. European Journal of Oral Sciences 1995 Apr. 103(2)(PT1):112–5.

*Primary Examiner*—Gene Mancene
*Assistant Examiner*—Pedro Philogene

[57] ABSTRACT

A method of treating oral and systemic diseases includes impregnating or coating a toothpick with active therapeutic agents and rubbing the toothpick against mouth tissue to release the active therapeutic agents onto the tissue for penetration through the tissue. The active therapeutic agent is selected from the group consisting of, but not limited to: zinc sulfate, zinc chloride, zinc acetate, zinc phenol sulfonate, zinc borate, zinc bromide, zinc nitrate, zinc glycerophosphate, zinc benzoate, zinc carbonate, zinc citrate, zinc hexafluorosilicate, zinc diacetate trihydrate, zinc oxide, zinc peroxide, zinc salicylate, zinc silicate, zinc stannate, zinc tannate, zinc titanate, zinc tetrafluoroborate, zinc gluconate, and zinc glycinate. An additional therapeutic agent may also be impregnated or coated on the toothpick, for example, antimicrobials, antibiotics, antioxidants, antiplaque agents, analgesics, anti-tartar agents, anti-caries agents, hemostatic agents, anti-inflammatory agents, hormones, bleaching agents, vitamins, vaccines, caffeine and monoclonal antibodies.

11 Claims, No Drawings

THERAPEUTIC TOOTHPICK FOR TREATING ORAL AND SYSTEMIC DISEASES

This application is a continuation-in-part of Ser. No. 08/935,841 filed Sep. 23, 1997, now pending.

FIELD OF THE INVENTION

The present invention relates to the therapeutic use of toothpicks. More particularly, the present invention relates to toothpicks impregnated or coated with therapeutic agents such as zinc salts, vitamins, antioxidants, fluoride salts, and other medicaments. Most particularly, the present invention relates to a novel toothpick formulation and related method for treating gingivitis and periodontal disease, that may predispose individuals to cardiovascular disease, premature births, HIV transmission, atherosclerosis, arthritis, and other chronic diseases.

BACKGROUND OF THE INVENTION

Before the onset of disease, healthy pink gingiva (gum tissue) surrounds the teeth, both holding them in place and preventing infectious material from entering the jaw bone or tooth itself. The tooth includes three regions known as the crown, neck, and root. Gingiva or gum tissue is the soft tissue covering the neck of the tooth. The area between the enamel and the gingiva is called the gingival crevice. The gums are under constant bacterial assault. Gingivitis develops when large masses of bacteria clog the gingival crevice.

Periodontal disease (gum disease) is one of the most prevalent chronic diseases affecting man. Children as young as 5 years of age can have gum disease. By age 35, three out of four people are affected, and by age 65, an estimated 98 percent of Americans have periodontal disease. Periodontal comes from two Greek words that mean "around the tooth." Periodontal disease is caused by certain types of bacteria that form a sticky, colorless film of bacteria that constantly forms on teeth called plaque. Plaque that is not removed can combine with other materials and harden into a rough, porous deposit called calculus (tartar). Calculus on the tooth surface (above the gum line) may not contribute to periodontal disease, but calculus on the neck or root surface (below the gums) makes removal of new plaque and bacteria more difficult. Bacteria in plaque produce metabolic by-products that diffuse into the immediate surrounding area, irritate the gingiva, and result in an inflammatory reaction. The gingiva then swells, become reddened, sensitive to touch and may bleed. It is not normal for gums to bleed when brushing or flossing. Bleeding gums is usually the first sign of gingivitis. Gingivitis is reversible. Gum disease occurs when the gingival crevice between the tooth and gum is more than three millimeters. As gingivitis progresses, the tissue surrounding the teeth is destroyed, the supporting collagen fibers begin to degenerate, and eventually the bone supporting the tooth socket degenerates and results in tooth loss.

Periodontal disease can be prevented by practicing good oral hygiene. Daily tooth brushing and flossing are the most important weapons against the formation of plaque. Brushing your teeth thoroughly at least twice a day helps remove plaque from the outer, inner, and chewing surfaces of the teeth. But careful brushing alone is not sufficient, simply because the bristles of the toothbrush cannot make contact with all parts or sides of the teeth. Dental floss helps to remove plaque from the crevices between the teeth that are often too deep to reach with any sort of brush. Toothpicks are pointed instruments used for removing food or other particles lodged at the base of or from between the teeth. Since manual dexterity decreases with increasing age, the use of toothpicks may be more convenient and require less effort than dental floss. Murtomaa H. Meurman J H, *International Dental Journal* 1992 Oct. 42(5):365–72.

Toothpicks are usually tapered to a point at one or both ends and are made of wood, plastic, stiff paper, metal, ivory or other materials that provide sufficient rigidity to expel particles between the teeth, yet narrow enough to fit into the interdental spaces. Toothpicks come is various shapes: straight, bent, round, flat, curved, and various combinations. Toothpicks are dispensed singularly, individually wrapped in plastic, in matchbook dispensers, in rolls to be broken off and used, and some are stored in containers. Stuart, U.S. Pat. No. 3,913,596 discloses a ribbon of stiff paper that separates into triangles to dislodge particles between the teeth. Freeman, U.S. Pat. No. 5,704,388 discloses a tubular toothpick formed from synthetic resin materials that has a defined feathered cleaning edge.

Some toothpicks claim the ability to contain different agents. Manciocchi, U.S. Pat. No. 4,509,541 discloses a toothpick attached to a hollow cylinder containing an antiseptic solution to wet the toothpick from a wick. Lichfield, U.S. Pat. No. 4,304,245 discloses a thin sheet of polymeric material rolled to form a tapered tube with a hollow core to remove blood or liquids and may also carry breath fresheners or medicines. Lichfield claims that wooden or plastic toothpicks are only useful for dislodging particles from the teeth, not delivering medications. Howard, U.S. Pat. No. Des. 335,934 discloses an ornamental design for a tobacco-impregnated toothpick. Johnson, U.S. Pat. No. Des. 358,682 discloses an ornamental design for a nicotine containing toothpick. Wiley, U.S. Pat. Nos. 4,846,200 and 5,002,077 discloses a periodontal pocket cleaner, which is a wooden device used to remove material from the periodontal pockets. Wiley differentiates his device from the toothpick and does not claim the toothpick capable of delivering medications.

Besides removing food particles, toothpicks have dental hygiene functions by stimulating gum tissue, removing plaque and calculus that accumulate on the tooth surface and help prevent caries. Toothpicks are usually provided by restaurants and more socially acceptable to use than dental floss.

Using dental floss to help remove plaque from the tooth surface is known in the art. Further, it is known in the art to apply substances and medicaments to dental floss. The substances applied to dental floss can also be applied to toothpicks. As an illustration, therapeutic dental floss has been developed for the following purposes:

Plaque Removal

The removal of plaque from teeth by the use of dentifrice formulations of toothpaste, gels, mouthwashes and dental floss is well described in the literature. For example, Lynch, U.S. Pat. Nos. 4,632,937 and 4,627,975 discloses coating the dental floss with a solution of monoalkyl and dialkyl ethers of dianhydrohexitols to reduce plaque accumulation. Wilkinson, U.S. Pat. No. 4,819,675 discloses impregnating the dental floss with potassium hydrogen tartrate and potassium hydrogen citrate to remove plaque formation. Curtis, U.S. Pat. No. 5,033,488 discloses the use of anti-plaque agents such as chlorhexidine, hexachworaphene, cetylpyridinium chloride and benzothonium chloride, coated on polytetrafluoroethylene dental floss. The dental cleaning floss may also contain a coagulating agent, fluoride and anti-tartar agents such as tetrasodium pyrophosphate, sodium acid pyrophosphate or tetra potassium pyrophosphate. Greene, U.S. Pat. No. 5,065,861 discloses a dental floss dispenser in which baking soda and hydrogen peroxide attach to roughened dental floss as it is pulled out of the container.

Germicidal Agents

Dental floss has also been coated with germicidal agents to attack the microorganisms in the mouth. Corliss, U.S. Pat. No. 3,942,539 discloses dental floss pre-soaked with an antiseptic mouthwash solution. Rosenberger, U.S. Pat. Nos. 5,040,554, 5,280,796 and Re. 35,439 discloses dental floss coated with sodium phenolate or 4-hexylresorcinol. In Britton, U.S. Pat. No. 5,226,434 it is disclosed that the anti-bacterial agent chlorhexidine is coated on the dental floss. Ahlert, U.S. Pat. No. 5,423,337 discloses the use of micro encapsulated calcium peroxide. Bowen, U.S. Pat. No. 5,603,921 discloses dental floss coated with chiorhexidine gluconate.

Antibiotics

Dental floss had also been coated with antibiotics. Hill, U.S. Pat. No. 5,098,711 discloses dental floss containing tetracycline, chlorhexidine, and polyvinyl pyrrolidone iodine complex as agents. Keller, U.S. Pat. Nos. 5,129,824 and 5,330,357 discloses tufted dental floss containing tetracycline.

Fluoride

The use of fluoride coated dental floss to inhibit the formation of dental caries is well known in the art. Guyton, U.S. Pat. No. 4,029,113 discloses the use of a fluorine compound coated on dental floss. Yost, U.S. Pat. No. 4,414,990 discloses the use of a fluoride salt on dental floss. Newmann, U.S. Pat. Nos. 4,548,219 and 4,638,823 disclose the use of fluoride-coated dental floss. VanBeneden, U.S. Pat. No. 4,941,487 discloses a dental floss with patches of fluoride. Curtis, U.S. Pat. Nos. 5,033,488 and 5,209,251 discloses a dental cleaning floss containing a dentifrice, preferably a fluoride. Bottled water consumption has dramatically increased in the U.S., and is the usual source of drinking water in the world. The lack of fluoride in most bottled waters may lead to an increased risk of tooth decay. The use of fluoride salts on toothpicks could overcome that deficiency. A recent study compared the use of a fluoride impregnated toothpick, fluoride mouth rinse, sucking a fluoride tablet and fluoride containing toothpaste. The highest concentration of fluoride in the saliva was obtained after using the fluoridated toothpick. Kashani H et al. *European Journal of Oral Sciences* 1995 Apr. 103(2)(Pt 1): 112-5.

Hemostatic Agents

Gingivitis frequently causes bleeding of the gums and hemostatic agents have been applied to dental floss. Vlock, U.S. Pat. No. 4,937,066 discloses the use of a dentifrice containing heavy metal salts to stop bleeding. Fisher, U.S. Pat. No. 5,635,162 discloses the use of a dentifrice containing heavy metal salts to maintain hemostasis. Curtis, U.S. Pat. Nos. 5,033,488 and 5,209,251 discloses the use of polytetrafluorethylene as floss material and adds hemostatic agents.

Zinc Salts

Zinc is a trace element and essential for biologic functions such as growth, appetite, testicular maturation, skin integrity, mental activity, wound healing, and maintaining the immune system. Zinc compounds have a long history of use as antiplaque and antitartar agents in toothpaste, gels and mouthwashes, as disclosed by Vinson in U.S. Pat. No. 4,022,880, Richey in U.S. Pat. No. 4,647,452 and Douglas in U.S. Pat. No. 5,104,644, but not as zinc coated dental floss or toothpicks for those purposes. Sipos, U.S. Pat. No. 4,160,821 discloses the use of zinc salts as a toothpaste to treat gingivitis. He noted that zinc chloride has been used as an astringent to achieve gingival retraction after swelling and that zinc acetate used as a mouth rinse can cause plaque to disappear. Fahim, U.S. Pat. No. 4,229,430 discloses a mouthwash composed of a zinc salt and ascorbic acid to treat gingivitis and periodontal disease. Shah, U.S. Pat. No. 4,325,939 discloses the use of sodium zinc citrate as a toothpaste, mouthwash or chewing gum to remove plaque and tartar from the teeth. Fisher, U.S. Pat. No. 5,625,162 discloses the use of zinc tartrate complexes in toothpaste and mouthwash to treat gingivitis and prevent gum bleeding. Williams, U.S. Pat. Nos. 5,456,902, 5,616,313, and 5,632,972 discloses the use of zinc salts in toothpastes and mouthwashes to treat gingivitis.

Zinc is an essential mineral found in every form of life on earth. Unlike other metals, zinc is virtually nontoxic. Zinc and its compounds have long been recognized as possessing certain therapeutic functions. Zinc compounds are acknowledged as astringents and beneficial in wound healing, reducing inflammation, and has antimicrobial, antifungal and antiviral activity. Zinc is the active agent in formulations to treat diaper rash, decubitus ulcers, and abrasions. Zinc stabilizes the cell membranes and inhibits the formation of free radicals. Zinc also strengthens the integrity of blood vessel walls by reducing the membrane permeability and stopping bleeding. Zinc acetate is used in eye drops to relieve chronic inflammation of the cornea in conjunctivitis. Zinc is believed to act as a protease inhibitor in its effect against rhinovirus infections that cause the common cold. Eby in U.S. Pat. Nos. 4,503,070, 4,956,385, Re 33,465, 5,095,035, and 5,409,905 uses zinc salts in lozenges as a cure for the common cold, due to the effect of zinc ions on viruses. Eby noted that zinc ions protect cell plasma membranes against damage induced by cytotoxic agents, and that zinc ions harden the cement substance of capillary epithelium so that pathological transcapillary movements of plasma protein is inhibited and local edema, inflammation and exudation are thereby reduced. Douglas, U.S. Pat. No. 5,104,644 discloses a mouth rinse containing the antimicrobial, zinc chloride, that has antiplaque, antitartar, and anti-inflammatory actions. He noted that zinc salts reduce gum swelling and reduce inflammation. Zinc salts attach to the cell wall of microorganisms and prevent them from adhering to each other and attaching to the tooth surface, thus preventing plaque from forming. Zinc has also been shown to inhibit acid production by microorganisms, thus impeding decalcification of the tooth. Zinc ions appear to inactivate the biochemical transport mechanisms of microorganisms by inhibiting the formation of ATP. Kelly, U.S. Pat. No. 5,624,675 discloses that zinc salts used in a genital lubricant can kill HIV-infected lymphocytes.

Zinc salts have been shown to be effective against the causes of gingivitis and periodontal disease. This is significant because it is now believed that periodontal disease can lead to other systemic diseases. Periodontal disease, usually a chronic Gram-negative infection, represent a previously unrecognized risk factor for atherosclerosis and thromboembolic events. Previous studies have demonstrated as association between periodontal disease severity and the risk of coronary heart disease and stroke. Researchers believe that periodontal disease, once established, provides a biological burden of endotoxin (lipopolysaccharide) and inflammatory cytokines (especially $TxA_2$, IL-1 beta, $PGE_2$, and TNF-alpha) which serve to initiate and exacerbate atherogenesis and thromboembolic events. Beck J, et al, *J. Periodontol* 1996;67: 1123–1137. A study by the National Institutes of Health, led by Dr. Robert Genco, professor and chairman of Periodontology at the State University of New York suggest that infection and inflammation caused by gum disease may increase the risk of heart disease and that the inflammation caused by gum disease can contribute to the development of fatty plaque in heart arteries. The Health Professionals Follow-Up Study included a US national sample of 44,119 male health professionals (58% of whom were dentists) showed that those men who reported pre-existing periodontal disease had an increased risk of coronary heart disease. Joshipura K J, *J Dent Res* 1996 Sep;75(9):1631–6. Smoking, subgingival microorganisms and diabetes mellitus are risk factors for periodontal disease, which may confer risk for coronary heart disease and pre-term low birth weight. Papapanou PN, *Ann Periodontol* 1996 Nov;1(1): 1–36.

Untreated periodontal disease may account for a large proportion of premature births. Periodontal infection may account for as many as 18 percent of the 250,000 premature babies that are born weighing less than 5.5 pounds in the United States each year. If such births could be prevented by proper periodontal care and treatment of periodontal disease in women of childbearing age (18 to 34 years) the researchers stated that premature births might be reduced by abut 45,500 each year at a savings of almost $1 billion in intensive neonatal care. The bacteria found in periodontal disease appear to retard fetal growth by releasing into the woman's bloodstream toxins that reach the placenta and interfere with fetal development. In addition, the infection stimulates the woman's body to produce inflammatory chemicals, similar to those used to induce abortion, that can cause the cervix to dilate and set offuterine contractions. The risk of having a premature baby of low birth weight was at least 7.5 times as high for women with severe periodontal disease, and occurred in 5 percent of pregnancies and cost the country $5.7 billion a year. Offenbacher S, *J. Periodontol* 1996 Oct;67(10Suppl): 1103–13. While a birth weight of less than 3.3 pounds is a risk factor for cerebral palsy, findings suggest that maternal infections may account for 12 percent of cerebral palsy cases among children of normal birth weight. Grether J K, *JAMA* 1997;278:207–211.

A study involving insulin-dependent diabetics showed an association between renal disease, cardiovascular complications and periodontal disease. Thorstensson H, *J Clin Periodontol* 1996 Mar;23(3 Pt 1): 194–202. Periodontal disease has serious implications for other chronic diseases.

There are approximately 500,000 cases of AIDS reported to the Centers for Disease Control and Prevention (CDC) in Atlanta. A recent case documented HIV transmission from kissing. Researchers believe that blood from the man's bleeding gums was the source of the virus that entered the woman's bloodstream via her gum disease. CDC Morbidity and Mortality Weekly Report (1997;46:620–623). Zinc salts have both an astringent effect on gum tissue by decreasing swelling and bleeding and also an antiviral effect.

None of the foregoing patents mention or suggest the application of zinc salts to toothpicks as a means of directly preventing and treating gingivitis and periodontal disease and subsequently preventing the development of other systemic diseases. In a preferred form of the invention, the toothpick is impregnated or coated with a zinc salt such as zinc acetate or zinc gluconate. Zinc salts are selected from a group consisting of, but not limited to: zinc sulfate, zinc chloride, zinc acetate, zinc phenol sulfonate, zinc borate, zinc bromide, zinc nitrate, zinc glycerophosphate, zinc benzoate, zinc carbonate, zinc citrate, zinc hexafluorosilicate, zinc diacetate trihydrate, zinc oxide, zinc peroxide, zinc salicylate, zinc silicate, zinc stannate, zinc tannate, zinc titanate, zinc tetrafluoroborate, zinc gluconate, and zinc glycinate.

Antioxidants

Antioxidants enhance the healing of infected and noninfected wounds by reducing the damage caused by oxygen radicals. Injured gum tissues undergo free radical reactions more quickly than do healthy ones. It has been suggested that free radicals play a role in collagen destruction in periodontal disease. Antioxidants are the main host defense produced in response to the production of free radicals. Antioxidant defense mechanisms include but are not limited to: vitamin E, pyruvate Bcarotene, selenium, N-acetylcysteine, vitamin C, antioxyenzymes such as superoxide dismutase (SOD), catalase, glutathione peroxidase, and glutathione reductase together with the enzymes of the pentose monophosphate shunt pathway that regenerate NADPH. Pyruvate is one of the few antioxidants that readily enter cells, making it an ideal cytoplasmic antioxidant. Pyruvate alone or in combination with alpha tocopherol, vitamin E, inhibits reactive oxygen-induced damage. Vitamin E, a term that encompasses a small group of related tocopherols, is the major lipid-soluble antioxidant responsible for protecting the polyunsaturated fatty acids in membranes against lipid peroxidation. Tocopherols protect lipids by scavenging peroxyl radicals precluding further chain propagating steps. One or more antioxidants could be combined with the zinc salt to be impregnated or coated on the toothpick.

Other Active Agents

Other active components may be added to the toothpick to achieve the desired therapeutic effects. Individuals over 50 years of age need to supplement their diets with at least 25 micrograms of vitamin B-12 each day. If taken orally in a tablet with other vitamins or minerals the vitamin B-12 is destroyed by the stomach acids. One solution is to incorporate the vitamin B-12 onto the toothpick.

Studies have shown that postmenopausal women taking estrogen replacement therapy (ERT) tend to retain their teeth. ERT has been shown to strengthen bones by slowing the rate of loss of bone mineral. The incorporation of estrogen into the toothpick could strengthen the jawbone that supports the teeth.

In the 1980s the concept of locally delivering antibiotics to the periodontal pocket was introduced, and subsequent clinical trials have indicated that it is possible to reduce pocket depth and inflammation with tetracycline locally delivered to the periodontal pocket. Tetracycline is an inhibitor of collagenase, which destroys periodontal tissues. Clinical studies have also shown that it is possible to slow periodontal disease progression with non-steroidal anti-inflammatory medications such as flubiprofen, naproxen, ketoprofen and aspirin. Williams R C, *J Clin Periodontol* 1996 Mar;23(3 Pt 2):299–305. Systemically administered aspirin has been shown to reduce gingival inflammation and gingival crevice depth. Flemming T F, *J Clin Periodontol* 1996 Mar;23(3 Pt 1):153–9. Aspirin interferes with prostaglandin H2 synthase, the enzyme the body uses to manufacture prostaglandin. Prostaglandins are natural chemicals in the body that cause fever, headaches and inflammation. The addition of aspirin and/or antibiotics to toothpicks could be used to treat periodontal disease.

The applicant believes that inflammation is the main etiology in the develolpment of atherosclerosis, heart disease, stroke and diabetes. Anti-inflammatory agents, antibiotics, vaccines and monoclonal antibodies introduced into the oral cavity via a toothpick may reduce the incidence of systemic diseases.

The toothpick can be used as a delivery vehicle and could be impregnated or coated with various agents, among those: vaccines, caffeine, and monoclonal antibodies, such as streptococcus mutans adhesion protein, a key protein in the development of dental caries.

SUMMARY OF THE INVENTION

The present invention relates to toothpicks impregnated or coated with therapeutic agents. In particular this invention relates to the use of toothpicks containing zinc salts to treat gingivitis and periodontal disease that may predispose individuals to cardiovascular disease, premature births, HIV transmission, atherosclerosis, and other systemic diseases. The present invention also contemplates the addition of antioxidants, vitamins, fluoride salts, and other medicaments to the zinc treated toothpick.

DETAILED DESCRIPTION OF THE INVENTION

The dental profession is well aware of the value of the mechanical action of toothpicks to clean out food debris and remove dental plaque. Toothpicks alone remove plaque, but do not treat gingivitis or periodontal disease. Coating or impregnating the toothpick with a zinc salt and other therapeutic agents facilitates direct absorption of the medicaments by the periodontal tissues as the active material is wiped off the toothpick and onto the interdental spaces and gums. The toothpick of this invention allows the patient to self-administer the therapeutic agents directly to the periodontal tissues and treat the gingivitis and periodontal disease, and thus help prevent systemic diseases from occurring.

The toothpick used herein can be made of wood, plastic, stiff paper, metal, ivory or other materials that provide sufficient rigidity to expel particles between the teeth, yet narrow enough to fit into the interdental spaces. They come is various shapes: straight, bent, round, flat, curved and dispensed singularly, wrapped in plastic, in matchbook dispensers, in rolls to be broken off and used, some that are stored in containers and others known to the art.

The amount of therapeutic agents available to be transferred from the toothpick to the oral tissues will vary dependant on whether the agents are impregnated within wood or coated on plastic or other materials. The concentration of therapeutic agents can be either increased or decreased in order to reduce or increase the duration of effect oftreatment or the amount of the application. Many methods of treating the toothpicks are contemplated by the present invention.

The active therapeutic materials consist of zinc salts, antioxidants, fluoride salts, and other medicaments. Zinc salts are selected from a group consisting of, but not limited to: zinc sulfate, zinc chloride, zinc acetate, zinc phenol sulfonate, zinc borate, zinc bromide, zinc nitrate, zinc glycerophosphate, zinc benzoate, zinc carbonate, zinc citrate, zinc hexafluorosilicate, zinc diacetate trihydrate, zinc oxide, zinc peroxide, zinc salicylate, zinc silicate, zinc stannate, zinc tannate, zinc titanate, zinc tetrafluoroborate, zinc gluconate, and zinc glycinate. Antioxidants include but are not limited to: vitamin A, vitamin E, pyruvate B-carotene, selenium, N-acetylcysteine, vitamin C, superoxide dismutase (SOD), catalase, glutathione peroxidase, and glutathione reductase. Vitamin E encompasses a small group of related tocopherols. Fluoride salts are selected from a group consisting of, but not limited to: sodium fluoride, stannous fluoride, sodium monofluorophosphate, amine fluoride, or any other suitable fluoride salt which is readily soluble in an aqueous environment.

A carrier or binder can be mixed with the zinc salt and other therapeutic agents which will either speed or slow its passage through the oral tissues and into the bloodstream. The amount of active material in the coating can be varied according to desired end use. For treating gingivitis and periodontal disease the concentration of the therapeutic agent(s) will vary by weight, the remainder being binder with the exact amount dependent on the binder's properties, and in particular, the solubility of the active material therein.

The therapeutic agents may be encapsulated by means of microencapsulation techniques into small beads. Suitable encapsulation materials include, but are not limited to polymeric coatings such as ethylcellulose and other coating polymers which coat and preserve the active ingredient until released by mechanical action of the toothpick between teeth and by enzymatic action of the saliva in the mouth. Polymeric coatings which are useful in the present invention includes: alkyl monoesters of poly(methyl vinyl ether maleic acid), polyvinyl pyrrolidones, acrylaminde/acrylate/butylaminoethyl mathacrylate polymers, terpolymers, copolymers, terpolyamines, and hydroxypropyl cellulose. Alternatively, the toothpick may be impregnated with therapeutic agents and subsequently coated with a water-soluble cellulose derivative such as methyl cellulose or sodium carboxymethyl cellulose as a binder.

A surfactant may be selected from the group consisting of, but not limited to: sodium lauryl sulfate, sodium lauroyl sarcosinate, polyethylene glycol stearate, polyethylene glycol monostearate, coconut monoglyceride sulfonates, sodium alkyl sulfate, sodium alkyl sulfoacetates, copolymers of polyethylene and polybutylene, allypolyglycol, copolymers of polyoxybutylene and polysxylethylene.

To the mixture may also be added dyes, flavorings, detergents, polishing agents, sweeteners, pigments, antimicrobials, antibiotics, analgesics, bleaching agents, vitamins, vaccines, caffeine, monoclonal antibodies, and other antibacterial agents, such as those known to persons skilled in the art may be added to the zinc salt in amounts sufficient to impart their particular characteristic.

The above-mentioned patents are hereby incorporated by reference.

Many variations of the present invention will suggest themselves to those skilled in the art in light of the above-detailed description. For example, any zinc salt containing compound may be employed. Further, the toothpick employed may be of any type. All such obvious modifications are within the full intended scope of the appended claims.

What is claimed is:

1. A therapeutic toothpick for treatment of oral and systemic disease by absortion of therapeutic agents through periodontal tissue, comprising:
   a) a toothpick, tapered at least at one end, sufficiently to permit the tapered end of the toothpick to be placed between the teeth and gum, b) a saliva soluble coating near at least one end of the toothpick, said coating comprising;
  1) at least one therapeutic agent which releases ions on contact with the saliva, and
  2) a carrier that maintains the therapeutic agent on the toothpick until placed in contact with saliva,
wherein the absorption of the ions of the therapeutic agent in the saliva may be enhanced by placement of the tapered end between the teeth and gums, permitting the therapeutic agent to be absorbed into the bloodstream in amounts sufficient to treat systemic diseases.

2. The therapeutic toothpick of claim 1, wherein the toothpick is selected from a group capable of maintaining the therapeutic agent, consisting of wood, plastic, stiff paper, metal, ivory, or other materials and various shapes that provide sufficient rigidity to expel particles from between the teeth, yet narrow enough to fit into interdental spaces.

3. The therapeutic toothpick of claim 1, wherein the therapeutic agent is selected from a group consisting of, but not limited to: zinc chloride, zinc acetate, zinc phenol sulfonate, zinc borate, zinc bromide, zinc nitrate, zinc glycerophosphate, zinc benzoate, zinc carbonate, zinc citrate, zinc hexafluorosilicate, zinc diacetate trihydrate, zinc oxide, zinc peroxide, zinc salicylate, zinc silicate, zinc stannate, zinc tannate, zinc titanate, zinc tetrafluoroborate, zinc gluconate, and zinc glycinate.

4. The therapeutic toothpick of claim 1, further comprising:
  an additional therapeutic agent impregnated and maintained by the carrier, wherein the additional therapeutic agent is selected from the group consisting of: antimicrobials, antibiotics, antioxidants, anti-plaque agents, analgesics, anti-tartar agents, anti-caries agents, hemostatic agents, anti-inflammatory agents, hormones, bleaching agents, vitamins, vaccines, caffeine and monoclonal antibodies.

5. A method of treating oral and systemic diseases, comprising the steps of:
  impregnating and coating the toothpick with an active therapeutic agent which maintains the therapeutic agent on the toothpick until placed in contact with saliva, whereupon ions of the therapeutic agent are released into the saliva; onto the periodontal tissue for penetration through the tissue and then absorbed into the bloodstream to treat systemic diseases.

6. The method of claim 5, wherein the active therapeutic agent is a zinc salt.

7. The method of claim 5, wherein the active therapeutic agent is selected from a group consisting of, but not limited to: zinc sulfate, zinc chloride, zinc acctate, zinc phenol sulfonate, zinc borate, zinc bromide, zinc nitrate, zinc glycerophosphate, zinc benzoate, zinc carbonate, zinc citrate, zinc hexafluorosilicate, zinc diacetate trihydrate, zinc oxide, zinc peroxide, zinc salicylate, zinc silicate, zinc stannate, zinc tannate, zinc titanate, zinc tetrafluoroborae, zinc gluconate, and zinc glycinate.

8. The method of claim 5, further comprising the step of coating the toothpick with a carrier.

9. The method of claim 5, wherein the active therapeutic agent is impregnated and disbursed in the carrier and the carrier maintains the therapeutic agent on the toothpick until placed in contact with saliva, whereupon ions of the therapeutic agent are released into the saliva, and the ions of the therapeutic agent in the saliva are absorbed through the periodontal tissue upon contact with the ionized saliva and then absorbed into the bloodstream to treat systemic diseases.

10. The method of claim 9, wherein the toothpick is impregnated or coated with an additional therapeutic agent.

11. The method claim 5, further comprising the step of impregnating and coating the toothpick with an additional therapeutic agent maintained by the carrier is selected from the group consisting of: antimicrobials, antibiotics, antioxidants, anti-plaque agents, analgesics, anti-tartar agents, anti-caries agents, hemostatic agents, anti-inflammatory agents, hormones, bleaching agents, vitamins, vaccines, caffeine and monoclonal antibodies.

* * * * *